(12) United States Patent
Manassen

(10) Patent No.: US 8,508,748 B1
(45) Date of Patent: Aug. 13, 2013

(54) INSPECTION SYSTEM WITH FIBER COUPLED OCT FOCUSING

(75) Inventor: Amnon Manassen, Haifa (IL)

(73) Assignee: KLA-Tencor Corporation, Milpitas, CA (US)

( * ) Notice: Subject to any disclaimer, the term of this patent is extended or adjusted under 35 U.S.C. 154(b) by 406 days.

(21) Appl. No.: 12/793,527

(22) Filed: Jun. 3, 2010

(51) Int. Cl.
*G01B 9/02* (2006.01)
*G01B 11/02* (2006.01)

(52) U.S. Cl.
USPC .......................................... 356/479; 356/511

(58) Field of Classification Search
USPC ..................... 356/479, 497, 511–514, 516
See application file for complete search history.

(56) References Cited

U.S. PATENT DOCUMENTS

| | | | |
|---|---|---|---|
| 7,403,293 B2 * | 7/2008 | Pellemans et al. | 356/521 |
| 7,525,666 B2 * | 4/2009 | Lindner et al. | 356/511 |
| 7,760,364 B1 | 7/2010 | Zhuang | |
| 7,770,231 B2 | 8/2010 | Prater et al. | |
| 7,791,731 B2 * | 9/2010 | Kay | 356/450 |
| 7,869,057 B2 * | 1/2011 | De Groot | 356/511 |
| 7,888,663 B2 | 2/2011 | Zhou et al. | |
| 7,977,636 B2 | 7/2011 | Raschke | |
| 8,116,174 B2 | 2/2012 | Nishida et al. | |
| 8,209,767 B1 | 6/2012 | Manassen | |
| 2011/0321204 A1 | 12/2011 | Karaki et al. | |

* cited by examiner

*Primary Examiner* — Michael A Lyons
(74) *Attorney, Agent, or Firm* — Joshua D. Isenberg; JDI Patent

(57) ABSTRACT

An optical inspection system can include an optical coherent tomography (OCT) tool having an optical column with a beam splitter optically coupled to an objective. Illumination optics are coupled to the beam splitter. An OCT focusing system is optically coupled to the objective via the beam splitter. The OCT focusing system includes a broadband light source, a reflector, a photo-detector, all of which are connected by optical fiber to a fiber coupler in an interferometer configuration. The objective is optically coupled to the fiber coupler in the OCT focusing system by an optical fiber.

16 Claims, 5 Drawing Sheets

INSPECTION SYSTEM WITH FIBER COUPLED OCT FOCUSING

FIELD OF THE INVENTION

This invention generally relates to optical metrology and more particularly to an improved interferometer used in the inspection of a semiconductor substrate.

BACKGROUND OF THE INVENTION

Optical coherence tomography (OCT) is an optical signal acquisition and processing method. It captures micrometer-resolution, three-dimensional images from within optical scattering media (e.g., biological tissue). Optical coherence tomography is an interferometric technique, typically employing near-infrared light. The use of relatively long wavelength light allows it to penetrate into the scattering medium. Confocal microscopy, another similar technique, typically penetrates less deeply into the sample. An OCT system is essentially a broadband interferometer that is often used for depth section inspection of tissues in biological and medical applications.

Depending on the properties of the light source (superluminescent diodes and ultrashort pulsed lasers have been employed), Optical coherence tomography has achieved submicrometer resolution (with very wide-spectrum sources emitting over a ~100 nm wavelength range).

Optical coherence tomography is one of a class of optical tomographic techniques. A relatively recent implementation of optical coherence tomography, frequency-domain optical coherence tomography, provides advantages in signal-to-noise ratio, permitting faster signal acquisition. Optical Coherenced Tomography (OCT) is often used as an optical method in biology and medicine. Commercially available optical coherence tomography systems are employed in diverse applications, including art conservation and diagnostic medicine, notably in ophthalmology where it can be used to obtain detailed images from within the retina.

In inspection in general and optical metrology in particular there is an ever-increasing importance to the accurate determination of the sensing head distance from the inspected target. This is because of the frequent connection between system—target distance and overall measurement accuracy. As OCT operates essentially in the same way as a Linnik interferometer, OCT can be considered for use as a focus sensor like the Linnik interferometer.

FIG. 1 illustrates an example of a conventional metrology tool 100 that can be used to perform scatterometry measurements on the target structures at the surface of a sample 124. The metrology tool 100 may include a light source (not shown) optically coupled to illumination optics 114, potentially with angular/spatial dynamic control, for generating a probe beam 115 of radiation. The probe beam 115 may be turned towards the sample 124 with a 50/50 beam splitter 118. The probe beam 115 may be focused onto the surface of the sample 124 with a main objective 122. Probe beam radiation scattered from the target is collected and collimated by the objective 122 and at least a fraction of the sample beam passes through the beam splitter 118 and up an optical column of the tool 100. The fraction of the sample beam may be passed through relay lenses 104 and 106 and focused on an image detector 102, such as a charge-coupled device (CCD).

The metrology tool 100 includes an OCT focusing system having a second beam splitter 108, (sometimes called a focus beam splitter) a focus detector lens 110, a focus detector 112, a reference objective 120, and a reflector 121 that are arranged in a Linnik-type interferometer configuration. In a Linnik-type interferometer, the reference objective 120 has complementary optical properties to the main objective 122 so that the optical path length of the main and reference arms match.

A mechanical shutter 109 selectively opens and closes an optical path to the reference objective 120 between the beam splitter 118 and the reference objective 120, which focuses a reference beam onto the reflector 121. The reference beam passes back through the reference objective 120 toward the beam splitter 118.

Another fraction of the probe beam power (referred to as the sample beam) is reflected from the sample 124, and is directed toward the beam splitter 118 where it interferes with the reference beam. The resulting interference beam is directed to the focus beam splitter 108, which directs the interference beam towards the focus detector lens 110 which focuses the interference beam on a focus detector 112. Interference fringes are detected at the focus detector 112 as a result of interference between the sample beam and the reference beam. The interference fringes can be analyzed to detect whether the probe beam 115 is in focus at the sample 124.

However, OCT focus implemented as illustrated in FIG. 1 has some disadvantages. First, in a Linnik-type configuration the reference objective 120 has similar optical performance to the main objective 122 and is, therefore, expensive. The fringe quality depends on the optical matching between two complicated objectives (mainly limited by spherical aberrations). The mechanical shutter 109 is often a source of noise that can cause vibration. Because the interferometer is sensitive to temperature, the beam splitter must often be mounted with a piezoelectric tube (PZT) mount to compensate for temperature changes. This adds to the complexity and expense of the tool 100. Furthermore, because the focusing system uses the same illumination as is used for metrology, the spectrum available for focusing is constrained to the bandwidth used for metrology and does not enable the use of the widest possible spectral bandwidth for focusing. This is disadvantageous because a short coherence length is desired for the OCT-based focusing system and coherence length is inversely related to the bandwidth of the illumination used.

Furthermore, a Linnik interferometer configuration, such as that shown in FIG. 1, is sensitive to the system's environment, especially vibration which limits its precision. In addition, the need for a focus detector beam splitter has usually some effect on optical performance of the metrology tool that has to be monitored and calibrated away.

It is within this context that embodiments of the present invention arise.

BRIEF DESCRIPTION OF THE DRAWINGS

Objects and advantages of the invention will become apparent upon reading the following detailed description and upon reference to the accompanying drawings in which.

DESCRIPTION OF THE SPECIFIC EMBODIMENTS

Although the following detailed description contains many specific details for the purposes of illustration, anyone of ordinary skill in the art will appreciate that many variations and alterations to the following details are within the scope of the invention. Accordingly, the examples of embodiments of the invention described below are set forth without any loss of generality to, and without imposing limitations upon, the claimed invention.

Embodiments of the present invention are directed to inspection systems that incorporate an OCT focus system in a configuration with the potential for reduced cost and improved focus performance. The potential for reduced cost comes from avoiding the need for a reference objective and pzt-based beam splitter mount. In addition, the beam splitter 118 does not need to be precisely balanced in terms of optical path difference and the production cycle time for balancing the Linnik interferometer is not required. Improved performance may be achieved by locating the toggling mechanism for the OCT focus system remotely from the imaging head, thereby reducing mechanical coupling between the imaging and focusing systems. Another advantage of the remote positioning of the focus system is that the interferometer can be placed in a controlled environment (temperature, pressure, etc.) for improved precision. Furthermore, the focus illumination can also be toggled and posses a large bandwidth with reduced interferogram width contributing to improved focus accuracy. In addition, a performance-limiting focus detector beam splitter is not required in the imaging path.

Figure 1:
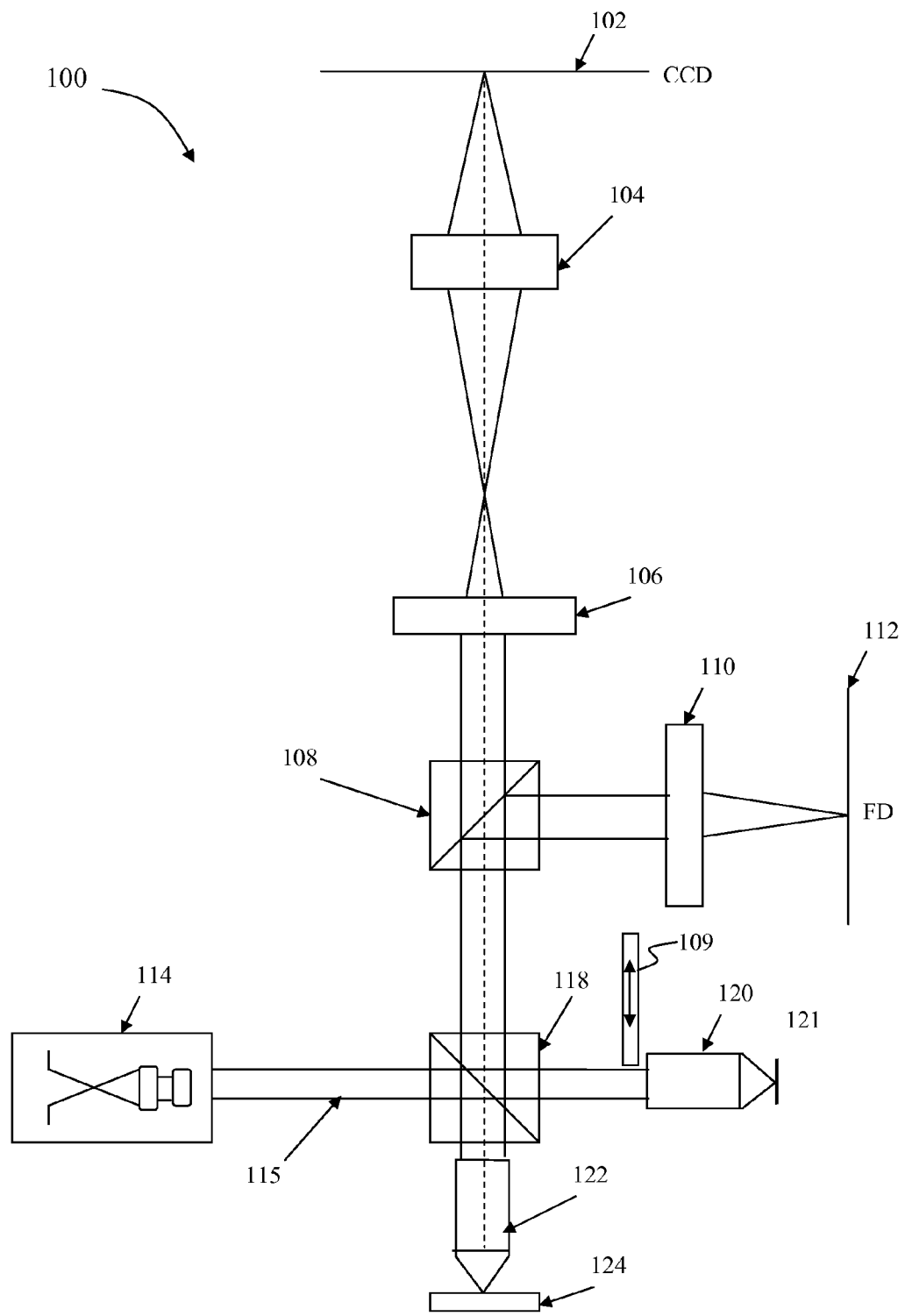
FIG. 1 is a schematic diagram illustrating a metrology to with a conventional Linnik focus system.
Figure 2:
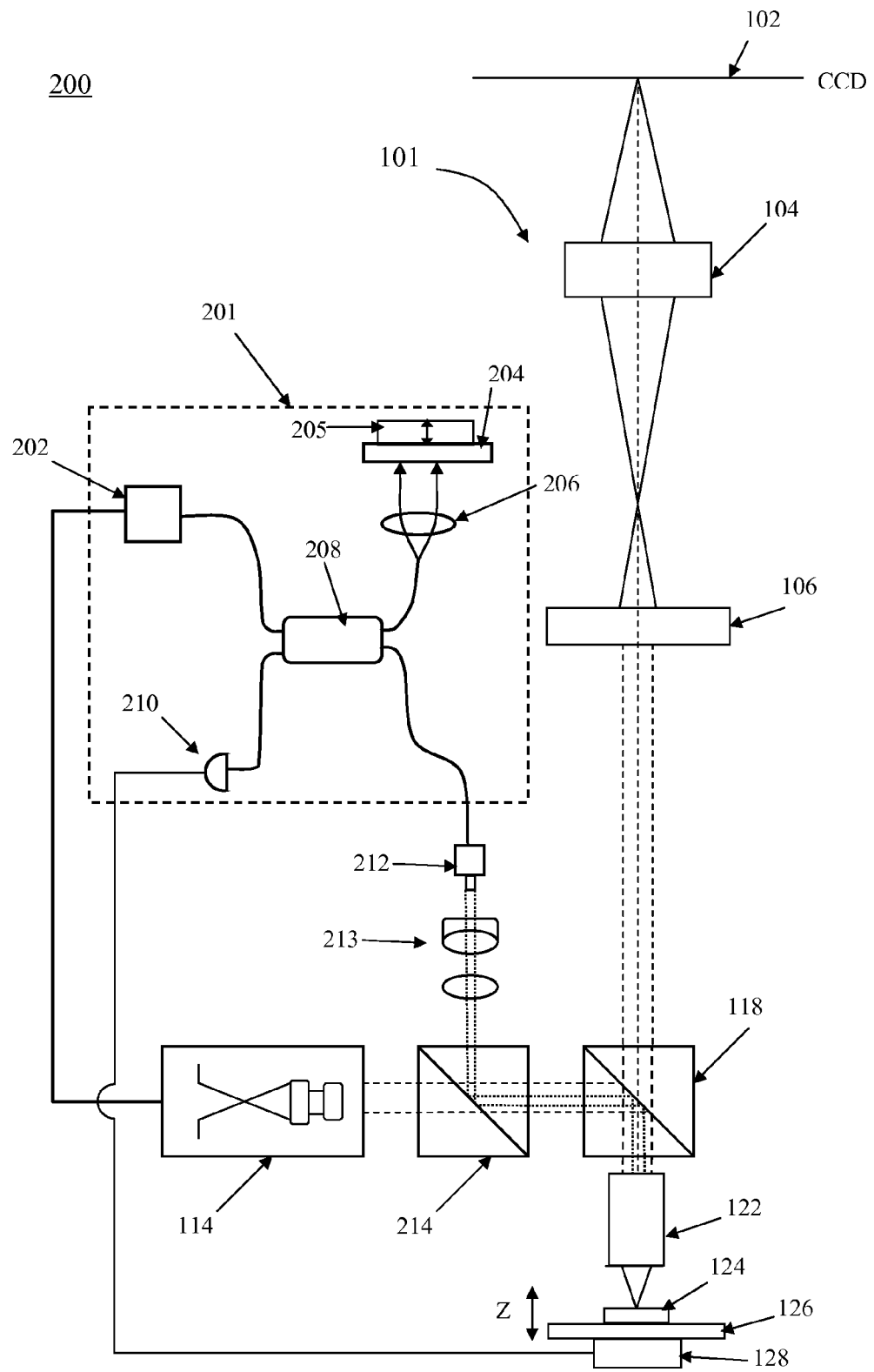
FIG. 2 is a schematic diagram illustrating a metrology tool with an OCT focus system in accordance with an embodiment of the present invention.

FIG. 2 is a schematic diagram illustrating an inspection system 200 according to an embodiment of the present invention. As shown in FIG. 2, the system 200 is similar to the metrology tool depicted in FIG. 1. The system 200 includes an imaging optical column 101 that includes an image detector 102, coupled by lenses 104 and 106 to a main objective 122. A beam splitter 118 couples light from illumination optics 114 to the objective 122. However, the inspection system 200 does not include the reference objective 120, the pzt-based beam splitter mount, the focus beam splitter 108, focus detector (FD) lens 110 and focus detector 112. Instead, the inspection system 200 includes an OCT focusing system 201 incorporated into the microscope's illumination system as an integral part. The OCT focusing system 201 includes a broadband light source 202, a reflector 204, a photo-detector 210, and a fiber collimator 212, all of which are connected by optical fiber to a fiber coupler 208. The reflector 204 can be mounted for translation, e.g., on a controllable piezoelectric tube (pzt) stage 205, to facilitate interferometer balancing. Other mechanisms for mounting the reflector 204 so that its position can be shifted in the direction indicated by the double arrow to facilitate interferometer balancing may alternatively be used. The broadband source 202 can be a low time-coherent light source such as a SuperContinuum source. As the OCT focusing accuracy benefits from a wide bandwidth it is ideal for use with a SuperContinuum source having a relatively flat spectrum in the range ~400 nm-2400 nm. (A smaller portion of the spectral range, e.g., 500-700 nm may be used for measurement illumination and a different range, e.g., 410-910 nm may be used for focusing). The broader wavelength range produces a shorter coherence length, which is often desirable in focus detection systems. The large brightness and throughput of a Supercontinuum source can support maximal bandwidth for focus operation along with visible range bandwidth for metrology. As the OCT employs in principle a similar concept to the current Linnik-based system, many of the current operating algorithms and methods can be used.

As shown in FIG. 2, a portion of the light from the broadband source 202 can be coupled to the reflector 204 via the fiber coupler 208 and a lens 206. Light coupled to the reflector 204 acts as a reference beam. The fiber coupler 208 can direct another portion of the light from the source 202 to the fiber collimator 212. Free-space optics 213 can couple the light from the fiber collimator 212 to an illumination beam splitter 214, which can be incorporated into the illumination optics 114 to couple light from the fiber collimator 212 to the beam splitter 118 in the optical column 101. It is noted that in the example depicted in FIG. 2, the broadband source 202 can be optically coupled to the illumination optics 114, e.g., by optical fiber. This allows the broadband source to provide illumination for focus detection and for sample inspection measurements. A separate light source (not shown) may be optically coupled to the illumination optics 114 to provide illumination for metrology measurements.

In operation, a portion of the light from the source 202 (referred to as the focus beam) is coupled to a sample 124 via the fiber coupler 208, the fiber collimator 212, free-space optics 213, beam splitters 214, 118, and the objective 122. At least a portion of the focus beam reflects off the sample 124 and couples back through the objective 122, beam splitters 118, 214, free-space optics 213, and fiber collimator 212 to the fiber coupler 208. The fiber coupler 208 couples the reflected portion of the focus beam to the photodetector 210, where the reflected focus beam and reference beam can interfere to produce fringes.

The photodetector 210 can be coupled in a suitably configured feedback loop to a stage translation mechanism 128 that moves the stage 126 in a Z direction along an optical axis of the objective 122. The translation mechanism moves the stage 126 in the Z direction to adjust the focus of the objective 122 on the sample 124.

By implementing the focus detector interferometer in fiber, the OCT focus system can be mechanically de-coupled from the optical column 101. This greatly simplifies the design of the optical column by eliminating the need for a reference objective and the reference beam splitter 108.

Figure 3:
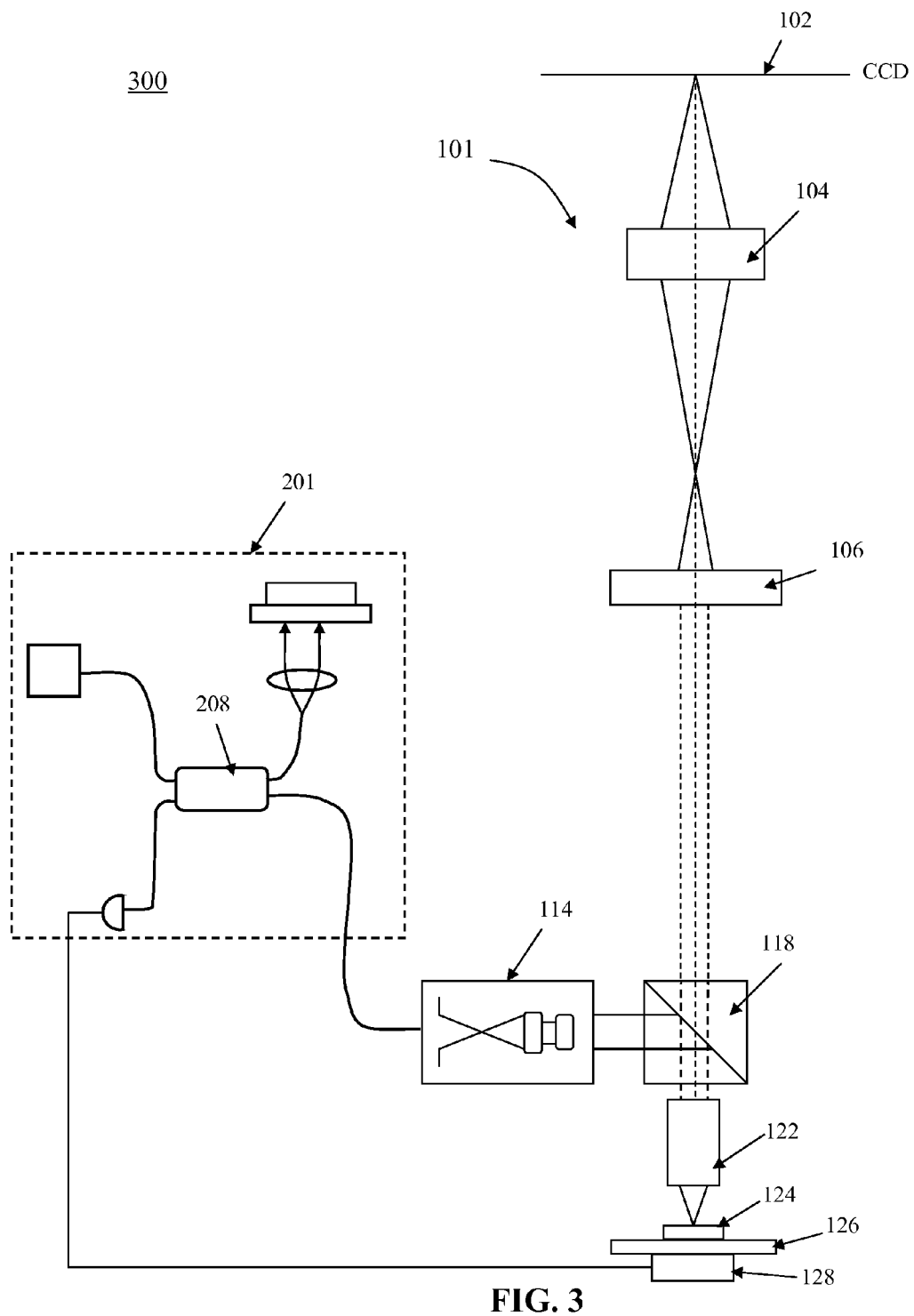
FIG. 3 is a schematic diagram illustrating a metrology tool with an OCT focus system in accordance with an alternative embodiment of the present invention.

There are a number of alternative configurations for incorporating a fiber-based OCT focusing system into an inspection system. FIG. 3 is a schematic diagram illustrating an inspection system 300 according to an alternative embodiment of the present invention. The system 300 is similar to the system 200 except that the OCT focusing system 201 is incorporated within illumination system. As shown in FIG. 3, the illumination system 114 is optically coupled to the fiber coupler 208 and directly to the beam splitter 118.

Figure 4:
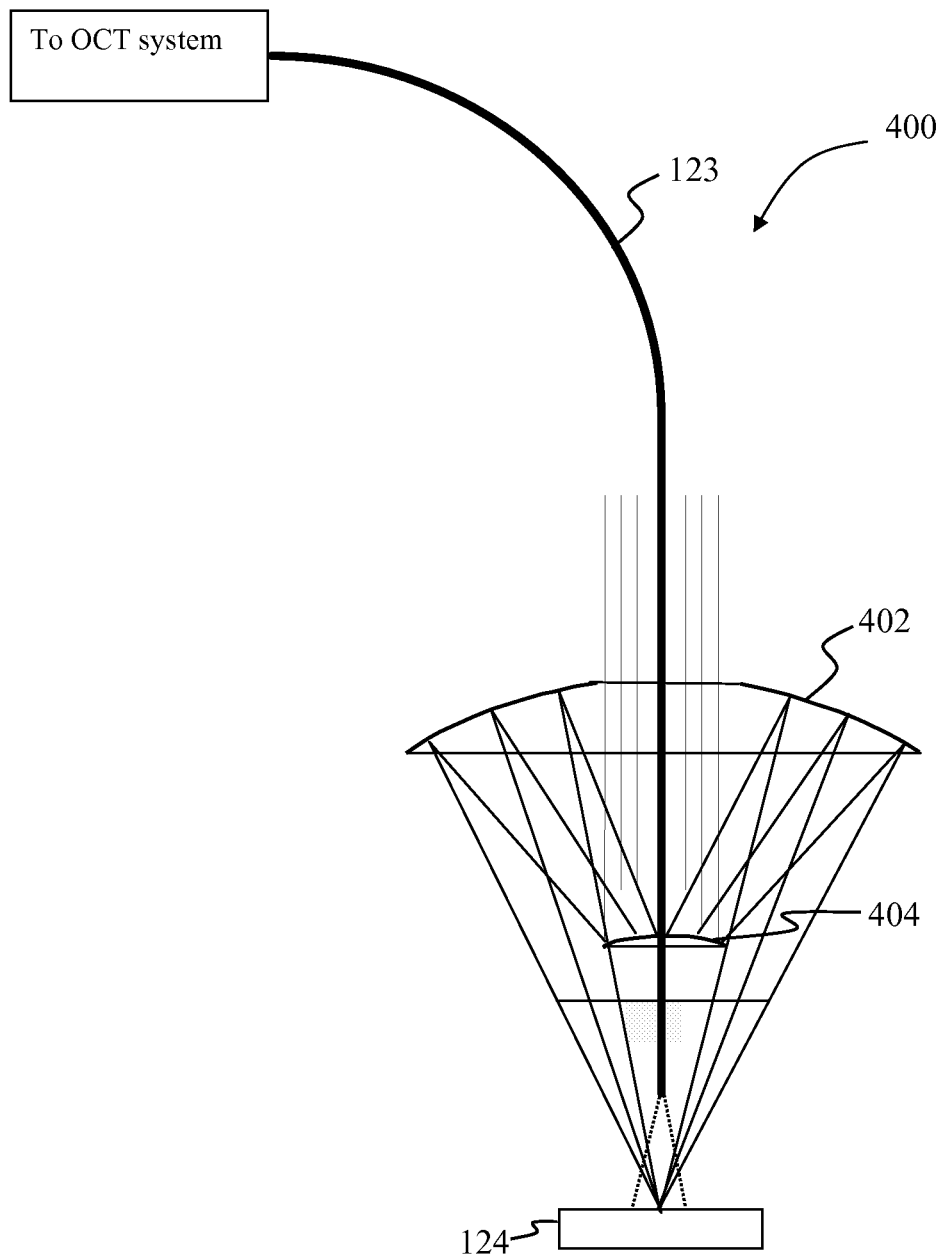
FIG. 4 is a schematic diagram illustrating a reflective objective that can be used in a metrology tool in accordance with an embodiment of the present invention.

FIG. 4 is a schematic diagram illustrating a reflective objective 400 that can be used in conjunction with certain embodiments of the present invention. The reflective objective 400 can include a primary mirror 402 and a secondary mirror 404 which can be rigidly fixed relative to each other by a frame. In this type of objective, the primary mirror 402 is a concave (focusing) mirror and the secondary mirror 404 is a convex (diverging) mirror. The primary and secondary mirrors are configured such that parallel light (e.g., illumination from the illumination optics) can reflect from the secondary mirror 404 towards the primary mirror 404, which focuses the light onto the sample 124. Equivalently, divergent light originating from the sample 124 can reflect from the primary mirror 402 towards the secondary mirror 404, which reflects the light as a parallel beam headed up the optical column.

As shown in FIG. 4, a dedicated fiber 123 can be introduced to the vicinity of the sample 124. The fiber introduction is done through a dedicated opening in a central obscuration of the objectives 400 obscuration, e.g., through an opening in the secondary mirror 404. A first end of the dedicated fiber can be optically coupled to the OCT focus system and a second end of the dedicated fiber can be located along an optical axis of the objective 400 between the secondary mirror 404 and a focal point of the objective 400. This type of the reflective objective 400 is useful for overlay and any metrology instrument that requires achromatic focus without introducing complexity in the design of the optics. The reflective objective 400 can be used with narrow bandwidth light.

Figure 5:
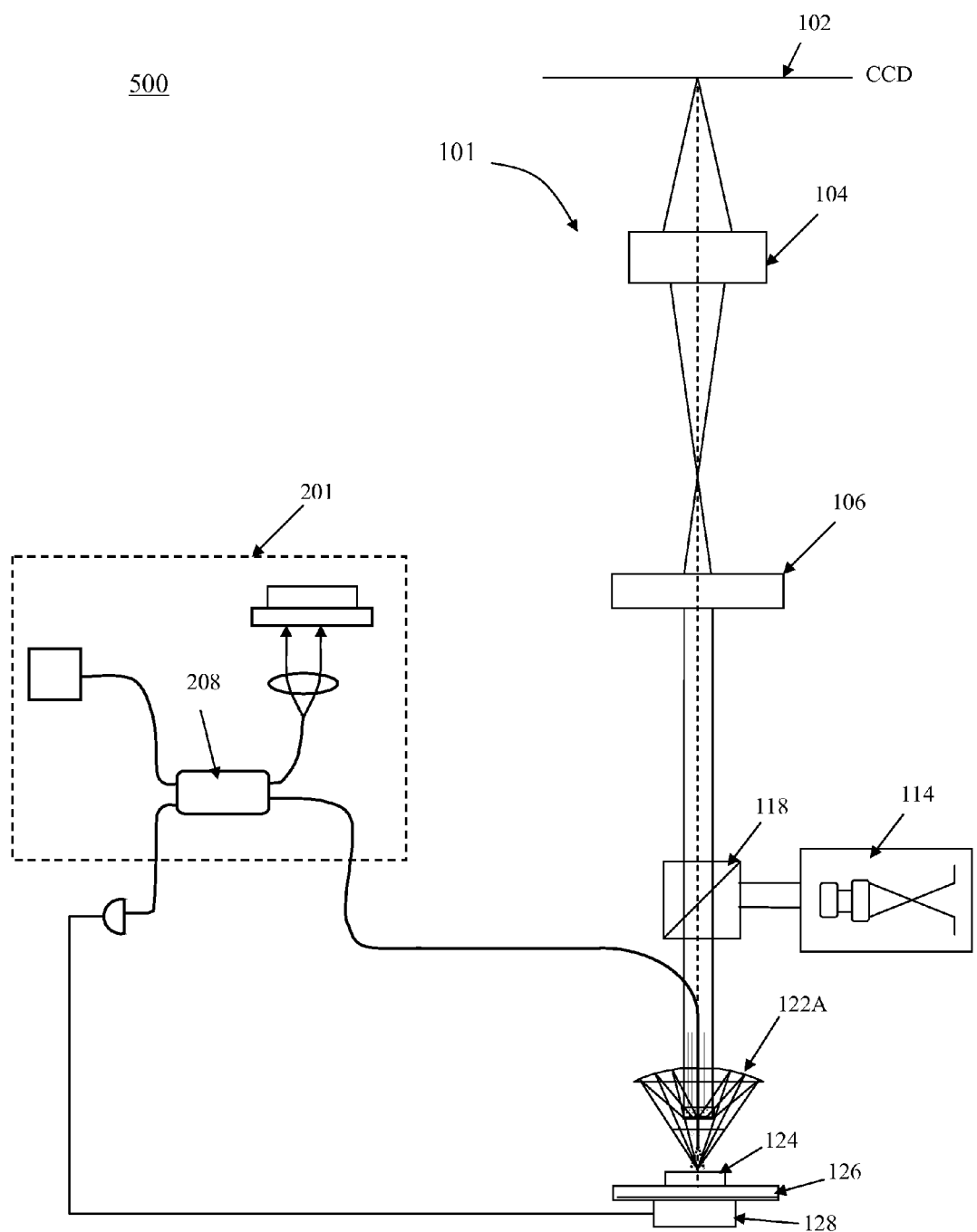
FIG. 5 is a schematic diagram illustrating metrology tool with an OCT focus system using a reflective objective of the type shown in FIG. 4 in accordance with an alternative embodiment of the present invention.

FIG. 5 is a schematic diagram illustrating an inspection system 500 according to an alternative embodiment of the present invention. The system 500 has many features in common with the systems depicted in FIG. 2 and FIG. 3 and described above. Specifically, the system includes an optical column 101, illumination optics 114, and OCT focusing system 201, which can be configured as discussed above. In this embodiment, the optical column 101 includes an objective 122A in the form of a reflective optical system, which may be configured like the reflective objective 400 described above with respect to FIG. 4. Similar to the system 200 of FIG. 2, the system 500 the optical column 101 can includes an image detector 102, coupled by lenses 104 and 106 to the objective 122A. A beam splitter 118 couples light from illumination optics 114 to the objective 122A. The objective 122A can be optically coupled to the OCT focusing system 201 by a dedicated optical fiber via the fiber coupler 208. In particular, a first end of the dedicated fiber 123 is optically coupled to the fiber coupler 208 and a second end of the dedicated fiber is located along an optical axis of the objective 122A between a central obscuration and a focal point of the objective.

Similar to system 200 in FIG. 2, a portion of the light from the broadband source 202 can be coupled to the reflector 204 via the fiber coupler 208 and a lens 206. Light coupled to the reflector 204 acts as a reference beam in an interferometer configuration.

In operation, a portion of the light from the source 202 (referred to as the focus beam) is coupled to a sample 124 via the fiber coupler 208 and the objective 122A. At least a portion of the focus beam reflects off the sample 124 and couples back through fiber 123 to the fiber coupler 208. The fiber coupler 208 couples the reflected portion of the focus beam to the photodetector 210, where the reflected focus beam and reference beam can interfere to produce fringes.

Since the beam splitter 118 does not require a pzt stage, a Z degree of freedom can be added to the stage that holds the sample and shifting elements can be avoided in the imaging channel. The above mentioned improvements in the imaging system are expected to improve robustness, mechanical tolerances and optical performance.

Another advantage for using the large bandwidth OCT system is the straightforward incorporation of such a system in a thin film inspection or metrology tool.

In the focusing phase of the metrology process, broadband illumination can flood the OCT and optical system. A sample stage 126 to which the sample 124 is mounted can be scanned in a Z direction causing detection of a narrow interferometric signal which in turn can be used to determine an optimal focus position. After focusing, the reference mirror 204 is scanned so that interferometric sectioning information about the sample 124 can be collected and analyzed. The robust optical system and environmentally controlled interferometer proposed here supports the achievement of sectioning information with high precision and accuracy.

The inspection systems of the present invention as described above have a lot of advantages compared with the conventional systems. First, a costly reference objective, beam splitter and beam splitter pzt stage are not required. Second, if a Z degree of freedom is added to the wafer stage, all shifting mechanisms can be stripped from the imaging system yielding reduced opto-mechanical tolerances and improved robustness. Third, the focus mechanism is located in a remote environment controlled enclosure. Fourth, reducing the imaging housing content, making it more robust and locating the vibration/temperature sensitive parts outside the measurement head is beneficial for integrated applications. Fifth, illumination source can also be toggled when focus system is switched into action, enabling broader spectrum in focusing resulting in improved accuracy. Sixth, the Focus Detector beam splitter in the imaging path is not required any more and thus the performance limitations of the beam splitter are avoided. Seventh, a thin film application can be added to the tool in a straightforward manner.

The reader's attention is directed to all papers and documents which are filed concurrently with this specification and which are open to public inspection with this specification, and the contents of all such papers and documents incorporated herein by reference.

All the features disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

While the above is a complete description of the preferred embodiment of the present invention, it is possible to use various alternatives, modifications and equivalents. Therefore, the scope of the present invention should be determined not with reference to the above description but should, instead, be determined with reference to the appended claims, along with their full scope of equivalents. Any feature, whether preferred or not, may be combined with any other feature, whether preferred or not. In the claims that follow, the indefinite article "A", or "An" refers to a quantity of one or more of the item following the article, except where expressly stated otherwise. The appended claims are not to be interpreted as including means-plus-function limitations, unless such a limitation is explicitly recited in a given claim using the phrase "means for."

What is claimed is:

1. An inspection system, comprising:
    an optical metrology tool having an optical column with a beam splitter optically coupled to an objective;
    illumination optics coupled to the beam splitter;
    an optical coherence tomography (OCT) focusing system having a broadband light source, a shiftable reflector, a photo-detector, all of which are connected by optical fiber to a fiber coupler in an interferometer configuration that is remote from the optical column, the OCT focusing system further including a fiber collimator optically coupled to the fiber coupler by an optical fiber, wherein the objective is optically coupled to the fiber coupler in the OCT focusing system by an optical fiber; and
    an illumination beam splitter optically coupled between the illumination optics and the beam splitter in the optical column, wherein the beam splitter is optically coupled to the fiber collimator, wherein the broadband light source is optically coupled to the illumination optics by a separate optical path that does not include the fiber coupler.

2. The inspection system of claim 1, wherein the illumination optics are directly coupled to the fiber coupler.

3. The inspection system of claim 1, wherein the objective includes a reflective objective.

4. The inspection system of claim 3, further comprising a dedicated optical fiber that passes through an opening in a central obscuration of the reflective objective, wherein a first end of the dedicated fiber is optically coupled to the fiber coupler and wherein a second end of the dedicated fiber is located along an optical axis of the objective between the central obscuration and a focal point of the objective.

5. The inspection system of claim 1, wherein the broadband light source comprises supercontinuum low time coherence light source.

6. The inspection system of claim 1, wherein a bandwidth of the broadband light source is broader than a bandwidth of radiation used to illuminate a sample via the illumination optics, the optical column beam splitter and the objective.

7. The inspection system of claim 1, wherein the OCT focusing system does not use an additional beam splitter in the optical column.

8. The inspection system of claim 1, further comprising a stage configured to hold a sample and a translation mechanism mechanically coupled to the stage, wherein the translation mechanism is configured to move the stage in a direction parallel to an optical axis of the objective.

9. The inspection system of claim 8, wherein the photo-detector is coupled in a feedback loop to the translation mechanism.

10. The inspection system of claim 1, wherein the metrology tool further comprises an image detector optically coupled to the objective.

11. An inspection system, comprising:
an optical metrology tool having an optical column with a beam splitter optically coupled to an objective, wherein the objective includes a reflective objective;
illumination optics coupled to the beam splitter;
an optical coherence tomography (OCT) focusing system having a broadband light source, a shiftable reflector, a photo-detector, all of which are connected by optical fiber to a fiber coupler in an interferometer configuration that is remote from the optical column;
a dedicated optical fiber that passes through an opening in a central obscuration of the reflective objective, wherein a first end of the dedicated fiber is optically coupled to the fiber coupler and wherein a second end of the dedicated fiber is located along an optical axis of the objective between the central obscuration and a focal point of the objective,
wherein the objective is optically coupled to the fiber coupler in the OCT focusing system by an optical fiber.

12. The inspection system of claim 7, wherein the broadband light source comprises supercontinuum low time coherence light source.

13. The inspection system of claim 12, wherein a bandwidth of the broadband light source is broader than a bandwidth of radiation used to illuminate a sample via the illumination optics, the optical column beam splitter and the objective.

14. The inspection system of claim 12, wherein the OCT focusing system does not use an additional beam splitter in the optical column.

15. The inspection system of claim 12, further comprising a stage configured to hold a sample and a translation mechanism mechanically coupled to the stage, wherein the translation mechanism is configured to move the stage in a direction parallel to an optical axis of the objective.

16. The inspection system of claim 15, wherein the photo-detector is coupled in a feedback loop to the translation mechanism.

* * * * *